United States Patent [19]
Fan et al.

[11] Patent Number: 5,558,900
[45] Date of Patent: Sep. 24, 1996

[54] ONE-STEP THROMBORESISTANT, LUBRICIOUS COATING

[76] Inventors: You-Ling Fan, 3 Heritage Ct., East Brunswick, N.J. 08816; Lawrence Marlin, 7 Wight St., Bridgewater, N.J. 08807

[21] Appl. No.: 310,723

[22] Filed: Sep. 22, 1994

[51] Int. Cl.$^6$ .............................. B05D 3/02; A61L 29/00
[52] U.S. Cl. .................... 427/2.28; 427/2.30; 427/374.5; 427/398.3
[58] Field of Search .................... 427/2.28, 2.30, 427/385.5, 393.5, 374.5, 353, 398.3

[56] References Cited

U.S. PATENT DOCUMENTS

| | | | |
|---|---|---|---|
| 3,642,943 | 2/1972 | Noel | 260/859 |
| 3,663,288 | 5/1972 | Miller | 117/7 |
| 4,055,682 | 10/1977 | Merrill | 427/2 |
| 4,098,933 | 7/1978 | Burkhardt et al. | 427/379 |
| 4,232,608 | 11/1980 | Wrightson | 102/103 |
| 4,265,927 | 5/1981 | Ericksson et al. | 427/2 |
| 4,315,091 | 2/1982 | Steinberger et al. | 427/393.5 |
| 4,327,009 | 4/1982 | Allen et al. | 524/114 |
| 4,373,009 | 2/1983 | Winn | 428/424 |
| 4,442,145 | 4/1984 | Probst et al. | 427/385.5 |
| 4,459,317 | 7/1984 | Lambert | 427/2 |
| 4,479,795 | 10/1984 | Mustacich | 604/53 |
| 4,487,808 | 12/1984 | Lambert | 428/423.1 |
| 4,513,112 | 4/1985 | Ernst et al. | 524/590 |
| 4,526,579 | 7/1985 | Ainpour | 604/265 |
| 4,585,666 | 4/1986 | Lambert | 427/2 |
| 4,589,873 | 5/1986 | Schwartz et al. | 427/2.3 |
| 4,592,920 | 6/1986 | Murtfeldt | 427/2.28 |
| 4,600,404 | 7/1986 | Sheldon et al. | 604/387 |
| 4,642,242 | 2/1987 | Solomon et al. | 427/2 |
| 4,666,437 | 5/1987 | Lambert | 427/2.28 |
| 4,729,914 | 3/1988 | Kliment et al. | 428/36 |
| 4,773,901 | 9/1988 | Norton | 604/265 |
| 4,876,126 | 10/1989 | Takemura et al. | 428/35.7 |
| 4,906,237 | 3/1990 | Johansson et al. | 604/265 |
| 4,980,231 | 12/1990 | Baker et al. | 428/36.9 |
| 4,987,181 | 1/1991 | Bichon et al. | 525/54.1 |
| 5,037,677 | 8/1991 | Halpern et al. | 427/338 |
| 5,041,100 | 8/1991 | Rowland et al. | 604/265 |
| 5,077,352 | 12/1991 | Elton | 525/409 |
| 5,084,315 | 1/1992 | Karimi et al. | 428/36.6 |
| 5,091,205 | 2/1992 | Fan | 427/2 |
| 5,135,516 | 8/1992 | Sahatjian et al. | 604/265 |
| 5,157,074 | 10/1992 | Metzger et al. | 427/389.8 |
| 5,235,018 | 8/1993 | Potter et al. | 528/49 |
| 5,268,397 | 12/1993 | Larson | 522/97 |
| 5,290,585 | 3/1994 | Elton | 427/2.3 |
| 5,295,978 | 3/1994 | Fan et al. | 604/265 |
| 5,342,556 | 8/1994 | Träubel et al. | 264/4.7 |

*Primary Examiner*—Diana Dudash
*Attorney, Agent, or Firm*—W. K. Volles

[57] ABSTRACT

A method of making articles having lubricious polymeric coatings are disclosed. The coatings are comprised of a substantially homogeneous composite of poly(ethylene oxide) and polyisocyanate applied in a single step operation as a mixture in an inert solvent. The coating is believed to form a polymeric complex through an in-situ hydrolysis of the polyisocyanate in the system without substantial crosslinking to form polyurethanes. The polymeric complexes have particular utility in providing medical devices such as catheters with a high degree of abrasion resistance and lubricity when in contact with bodily fluids.

9 Claims, No Drawings

ONE-STEP THROMBORESISTANT, LUBRICIOUS COATING

FIELD OF THE INVENTION

This invention relates to coating articles with a poly(ethylene oxide) and polyisocyanate coating. The coating is biocompatible and hydrophilic and can be used with particular advantage in the medical device and health care field.

BACKGROUND OF THE INVENTION

Catheters and guidewires which are used for insertion through blood vessels, urethra, or body conduits require a low-friction surface for preventing injury or inflammation of mucous membranes and for facilitating the surgical procedures. Conventional catheters have been rendered slippery by either construction with low-friction materials such as Teflon® and polyethylene, or substrates coated with a layer of Teflon®, silicone fluid, glycerin, or olive oil. These catheters are useful but not completely satisfactory because of either an inadequate retention of lubricity, or a lack of hydrophilicity. A variety of approaches have been undertaken in recent years to develop surfaces through either direct surface modification or the use of hydrogel coatings derived from different water soluble polymers (Y. L. Fan, *POLYMER NEWS*, March 1992, vol. 17,no. 3, pp 70–74). Poly(ethylene oxide) is one of the water-soluble polymers used for this purpose.

Poly(ethylene oxide) polymer is well known for its friction-reduction and blood-compatibility properties (R. L. Davidson, Handbook of Water-Soluble Gums and Resins, McGraw-Hill Book Co., New York, chapter; 19-1, 1980: M. Szycher, High Performance Biomaterials, Technomic Publishing Co., Lancaster, pp. 401–404, 1991).

Lambert in a series of U.S. Patents describes a two-step coating process to afford a lubricious coating by first applying an isocyanate coating and followed by a poly(ethylene oxide) coating (U.S. Pat. Nos. 4,585,666 and 4,459,317) and articles coated by his process (U.S. Pat. No. 4,487,808).

Elton describes a one-step coating process using a reactive coating mixture composed of an isocyanate, a polyol, and a poly(ethylene oxide) to cure the reactants and produce a urethane coating. A significant deficiency of the process is the limited time the mixed reactants can be stored after mixing due the high reactivity between an isocyanate and a polyol in the coating solution. A second deficiency of the process is the moderate lubricity of the urethane surface.

Rowland describes a coating with reduced friction produced from a structural plastic and a high molecular weight poly(ethylene oxide), U.S. Pat. No. 5,041,100. This process suffers from a lack of coating durability and uniformity. The poly(ethylene) oxide in the mixture may leach from the coating upon exposure to water resulting in a reduction in lubricity.

Notwithstanding the teachings of the above references, a need exists to provide a satisfactory one-step lubricious coating for medical devices.

SUMMARY OF THE INVENTION

The invention pertains to hydrophilic, coated articles produced by a one-step, thromboresistant, lubricious coating process where a mixture of a first polymer, poly(ethylene oxide), and a second polymer, polyisocyanate, in an inert solvent is used. By the process of this invention, an article, e.g., a medical device, is coated by first providing the above-mentioned solution. The article is then dried, e.g., baked in an oven, to finish the coating. The finished coating has a normal plastic feel when dry but becomes instantaneously lubricious upon exposure to body fluids.

The method for preparing the coated substrates comprises the steps of:

a) contacting a substrate with a solution of a polyisocyanate and a poly(ethylene oxide) said poly(ethylene oxide) having a molecular weight of from about 100,000 to about 8,000,000 grams per gram mole; and b) drying the coated substrate.

The invention surprisingly provides a more abrasion resistant coating utilizing a polyisocyanate/(polyethylene oxide) solution in a single step than the two step coating methods previously disclosed in the art. The hydrophilic coatings of the present invention comprise a substantially homogeneous composite of the poly(ethylene oxide) and the polyisocyanate polymers.

DETAILED DESCRIPTION OF THE INVENTION

Poly(ethylene oxide) polymers suitable for the purpose of this invention are represented by the following formula:

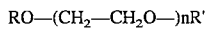

$$RO-(CH_2-CH_2O-)nR'$$

where R, R' is hydrogen or an alkyl, or aralkyl group containing from 1 to about 8 carbon atoms and n varies from about 2,000 to 200,000 such that the poly(ethylene oxide) polymers have a molecular weight ranging from about 100,000 to 8,000,000 grams per gram mole. As used herein, the term "molecular weight" means number average molecular weight. Methods for determining number average molecular weight are known to those skilled in the art. Examples of useful poly(ethylene oxide) polymers include POLYOX® WSR N-10, N-80, N-750, N-3,000, 3,333,205, 1105, N-12K, N-60K, 301, Coagulant, 303, and UCARFLOC® POLYMER 309. POLYOX® is a trademark for poly(ethylene oxide) produced by Union Carbide Corporation.

While poly(ethylene oxide) is an essential water-soluble polymer in the coating solution, other water-soluble polymers may be added, if so desired. Among these are poly(vinyl pyrrolidone), poly(ethylene glycol), methoxy poly(ethylene glycol), polyacryamide and poly(acrylic acid). As used herein, the term "coating solution" is intended to mean solutions aa well as dispersions and emulsions.

Preferably, however, the coating solutions of the present invention contain only minor amounts, i.e., less than about 5 weight percent, and more preferably are substantially free, i.e., less than about 1 weight percent, of polyols which can react with the polyisocynate to form polyurethanes, said percentages based on the total weight of the poly(ethylene oxide), polyisocyanate and said polyol.

Preferably, the resulting coatings of the present invention contain only minor amounts, i.e., less than about 5 weight percent, and more preferably are substantially free, i.e., less than about 1 weight percent, of polyurethanes, said percentages based on the total weight of the coating.

Other suitable additives in the coating solution include, but are not limited to, antimicrobial agents, antithrombogenic agents, and antibiotics. Details concerning the selection and amounts of such other ingredients are known to those skilled in the art.

Any multifunctional polyisocyanate may be used for the purpose of this invention with varying degrees of performance. Suitable useful polyisocyanates, include the monomeric polyisocyanates such as, toluene-2,3-diisocyanate, toluene-2,6-diisocyanate, m-phenylene diisocyanate, cyclohexylene-1,4-diisocyanate, 3,3-diphenyl-4-biphenylene diisocyanate, 4,4-biphenyl diisocyanate, 1,6-hexamethylene diisocyanate, 1,5-naphthalene diisocyanate, cumene-2,3-diisocyanate, 2,4-diisocyanatodiphenylether, 5,6-dimethyl-1,3-phenylenediisocyanate, 2,4-dimethyl-1,3 phenylenediisocyanate, 4,4-diisocyanatodiphenyether, 9,10-anthracene diisocyanate, 2,4-diisocyanatotoluene, 1,4-anthracene diisocyanate, 2,4,6-toluene triisocyanate, isophorone diisocyanate, and p,p', p"-triphenylmethane triisocyanate, and the like.

The preferred polyisocyanates are isocyanate end-capped prepolymers and adducts. Illustrative of isocyanate end-capped adducts are the reaction products of 2,4-tolylene diisocyanate, 4,4'-diphenylmethane diisocyanate, polymethylene polyphenyl isocyanate, or 1,5-naphthylene diisocyanate, with 1,2-polypropylene glycol, polytetramethylene ether glycol, 1,4-butanediol, 1,4-butylene glycol, 1,3-butylene glycol, poly(1,4-oxybutylene) glycol, caprolactone, adipic acid esters, phthalic anhydride, ethylene glycol, diethylene glycol, and other polyols used by urethane chemists for preparing prepolymers. Preferably, the polyioscyanate has a molecular weight of from about 100 to 10,000 grams per gram mole.

The most preferred polyisocyanates are polyisocyanurates derived from the trimerization of either aromatic or aliphatic diisocyanates. Examples of polyisocyanurates include the trimer of 2,4-tolylene diisocyanate or 4,4'-diphenylmethane diisocyanate or hexamethylene diisocyante or their mixtures.

The isocyanate end-capped prepolymers and adducts trimers of aromatic or aliphatic diisocyanates are preferred due to the enhanced performance characteristics of the resulting coatings.

For the purpose of this invention, the ratio of the poly(ethylene oxide) to the polyisocyanate in the mixture is important for the desired properties of the coating. Weight ratios of poly(ethylene oxide) to polyisocyanate from about 0.5/1 to about 125/1, preferably from about 2.5 to about 80/1, and most preferably from about 6/1 to about 20/1 are useful for the purpose of this invention. Since the equivalent weight of polyisocyanates varies, the corresponding weight ratios of poly(ethylene oxide) to active isocyanate will differ depending on the polyisocyanate employed. In general, weight ratios of poly(ethylene oxide) to active isocyanate is from about 3/1 to about 650/1, preferably from 10/1 to 400/1, most preferably from 30/1 to 125/1 are useful for the purpose of this invention. All weight ratios described herein refer to the composition of the initially prepared coating solutions. When the weight ratio of poly(ethylene oxide) to polyisocyanate is substantially below 0.5/1, the finished coating may not become lubricious when inserted into the body. When the weight ratio is substantially above 125/1, the finished coating may become insufficiently durable upon hydration.

Contrary to the disclosure of U.S. Pat. No. 5,077,352, no polyol is needed in accordance with this invention to provide a one step lubricious coating. Indeed, the process of the present invention does not involve a chemical reaction between a polyol and an isocyanate to form a urethane. Due to the high molecular weight poly(ethylene oxide) employed in this invention, any hydroxyl end groups on the poly(ethylene oxide) are expected to be insignificant in comparison to the polyisocyanate employed. While not bound by any mechanism, it is speculated that the unexpected excellent performance of the coating described in the present invention is due to the formation of a poly(ethylene oxide)/polyurea complex through in-situ hydrolysis of the polyisocyanate in the system. The hydrolysis may be induced by water present in the system or provided from an external source during drying or by the diffusion of atmospheric moisture to the coating to maintain equilibrium moisture content.

The solids content of the coating solution may vary widely depending on the type of poly(ethylene oxide) and polyisocyanate used such that the viscosity of the coating solution is adaptable to conventional solution coating processes. Typically, the viscosity of the coating solution is formulated to be below 500 centipoises, preferably below 200 centipoises and most preferably, below 50 centipoises. The total solids content of the coating solution may be as low as 0.1 to as high as 20 weight percent. Typically, the coating solution will contain from about 0.1 to 10 weight percent of poly(ethylene) oxide and from about 0.1 to 10 weight percent polyisocyanate based on the total weight of the coating solution.

Many inert organic solvents and mixtures thereof may be used in the preparation of the coating compositions of the present invention. Useful solvents include chlorinated aliphatic hydrocarbons, chlorinated aromatic hydrocarbons, acetonitrile, benzene, toluene, dimethylformamide, tetrahydrofuran, methylethyl ketone, xylene, anisole, 1,4 dioxane, ethylacetate, and their mixtures. The preferred solvents are chlorinated aliphatic hydrocarbons such as 1,2-dichloroehtane and dichloromethane most preferably 1,2-dichloroethane.

The one-step thromboresistant, lubricious coating of this invention is applied by a solution coating process, such as dip coating, roller coating, spray coating, and the like. In a dip coating process, a medical device such as a catheter, is first dipped in a coating bath containing this solution. A dwelling time of as short as one second to as long as one hour may be used depending on the material of construction of the device, the thickness of the coating to be applied to the substrate and the performance of the catheter. The wet catheter is removed from the bath and dried to remove the solvent e.g., by heating in a convection oven. A heating temperature of between about 30 to about 150 degrees centigrade, and a heating time of from about one minute to several hours may be used depending on the material of construction of the catheter, the type of polyisocyanate used, and the performance requirement of the finished article.

Optionally, the coated article may be quenched in an aqueous liquid. Typically, the aqueous liquid will comprise as least one other component such as, for example, poly(alkylene glycols) or alkoxypoly(alkylene glycols) having a molecular weight of about 100 to 30,000 grams per gram mole, preferably from about 100 to 20,000 grams per gram mole and more preferably from about 500 to 10,000 grams per gram mole. Preferably, the alkylene portion of the polyglycol comprises from about 2 to 4 and more preferably from about 2 to 3 carbon atoms per repeat unit. Preferably, the alkoxy portion of the polyglycol comprises alkyl groups having from 1 to 6 carbon atoms per molecule. Preferably, the poly(alkylene glycols) and alkoxy poly(alkylene glycols) are water soluble. As used herein, the term "water soluble" means that at least 1 weight percent of the glycol is soluble in water. The polyglycols can be homopolymers, e.g., poly(ethylene glycol), or copolymers, e.g., a copolymer of ethylene glycol and propylene glycol. Preferred poly(alkylene glycols) and alkoxy(polyalkylene glycols) have the formula:

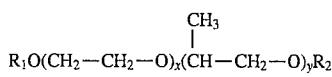

wherein:
(a) R1 and R2 can be the same or different and can be H or an alkyl group having 1 to about 6 carbon atoms;
(b) x is from 2 to about 500; and
(c) y is from 0 to about 100.

The poly(alkylene glycols) and alkoxy poly(alkylene glycols) may also contain functional groups such as, for example, hydroxyl, sulfur, nitrogen or oxygen. Poly(ethylene glycol) and methoxy poly(ethylene glycol) are particularly preferred. Other typical ingredients useful as an alternative to, or in addition to, the above mentioned glycols include, for example, phosphate salts of alkali metals or a mixture of one or more of the above.

The quenching step may be performed by any method used to coat the article. The quenching step may be incorporated to eliminate any residual isocyanate groups, to stabilize the coating and/or improve the coating's physical integrity against blocking or flaking or both. Blocking is defined as the bridging of adjacent coated surfaces in the presence of moisture or water which may result in damage done to the coated article during application such as the inflation of a folded balloon catheter typically employed in an angioplasty procedure or the contacting of a bundle of foley catheters during processing, packaging, shipping, etc.

Depending on the intended application of this coating, poly(alkylene glycol) or alkoxy poly(alkylene glycol) may be applied either as a sequential coating after the completion of the one-step thromboresistant, lubricious coating or preferably incorporated into the coating formulation directly when at least one end group on the poly(alkylene glycol) is alkyl. If incorporated in the coating formulation, alkyl poly(alkylene glycols) are preferred to avoid crosslinking the polyisocyanate/poly(ethylene oxide) coating. The coated article may be subsequently thermoformed and sterilized without adversely affecting its thromboresistant and lubricious properties.

The one-step thromboresistant, lubricious coating of this invention is expected to be broadly useful for modifying surfaces of various articles, such as, for example, medical devices including, but not limited to, catheters, guidewires, medical balloons, contact lenses, implant devices, intrauterine devices, peristaltic pump chambers, endotracheal tubes, gastroenteric feed tubes and arteriovenous shunts. The materials of construction of such articles is not critical to the present invention and may include materials such as, for example, polyolefins, e.g., polyethylene or polypropylene, polyurethane, polyester, nylon, elastomer, rubber, latex, poly(vinyl chloride), silicone polymer, ethylene copylmer, propylene copolymer, natural occurring polymers, and their derivatives.

Quite surprisingly, it has been found that the hydrophilic coatings of the present invention can provide enhanced properties, such as abrasion resistance, as compared to a coating made from the same materials applied as a two step process. The coatings provided by the present invention comprise a substantially homogeneous composite of the poly(ethylene oxide) and polyisocyanate, i.e., a uniform blend. Without being bound to any particular theory, it is believed that polymers in the composite are intertwined to a degree which enhances the complexing between the molecules during hydration, without any substantial crosslinking to form polyurethanes.

The Examples which follow are presented for the purpose of illustrating the invention and are not intended to limit the claims which follow limiting the claims. All parts and percentages are by weight unless otherwise specified.

The following terms are defined to have the following meaning in the pending examples:

| Chemical Purpose | Supplier | Chemical Composition | Purpose |
| --- | --- | --- | --- |
| POLYOX ® | Union Carbide Corp. Danbury, Ct. | Poly(ethylene) oxide | Coating Component |
| WSR N-10 | | MW 100 K** | |
| WSR N-80 | | MW 200 K | |
| WSR N-750 | | MW 300 K | |
| WSR N-3000 | | MW 400 K | |
| WSR 205 | | MW 600 K | |
| WSR 12K | | MW 1 MM | |
| WSR 60K | | MW 2 MM | |
| ISONATE 2181 | The Dow Chemical Company, Midland, MI | Polyisocyanate prepolymer, 23% Chemical | Coating Component |
| MONDUR ® TD | Miles Inc.* Pittsburgh, PA | Toluene diisocyanate, 48% (NCO) | Coating Component |
| MONDUR ® M | Miles Inc. | Diphenylmethane 4,4'-diisocyanate 33% (NCO) | |
| DESMODUR ® IL | Miles Inc. | Polyisocyanurate, 51% in n-butylacetate 8% (NCO) having a viscosity of 1200 to 2000 centipoises at 20° C. | |
| DESMODUR ® HL | Miles Inc. | Polyisocyanates, 60% in n-butyl acetate, 10.5% (NCO) having a viscosity of 1200 to 3200 centipoises at 23° C. | |
| MONDUR ® CB-60 | Miles Inc. | Aromatic polyisocyanate, 10.4% (NCO), 60% in PMA***/xylene | |
| MULTRON ® | Miles Inc. | Polyester | Coating |

-continued

| Chemical Purpose | Supplier | Chemical Composition | Purpose |
|---|---|---|---|
| R-18 | | polyol, OH Number 60 | Component |
| CARBOWAX ® M-PEG 350 | Union Carbide Corp. | Methoxy end-capped poly (ethylene oxide), MW350 | Additive |
| CARBOWAX ® M-PEG 5000 | Union Carbide Corp. | MW5000 | |

*Previously known as Mobay Chemical
**MW = molecular weight
**PMA = propylene glycol monomethyl ether acetate Description of Coating Makeup The coating solution exemplified in these examples may be prepared by any conventional mixing technique. For the preparation of laboratory quantities, it was convenient to use an explosion-proof Waring blender. The solvent dichloroethane was placed in a blender cup equipped with a cooling water jacket. The blender was turned on at a medium speed and poly(ethylene oxide) and polyisocyanate was added. The mixture was blended for about 5 to 10 minutes until the polymer was completely dissolved. A dear solution was usually obtained.

EXAMPLE 1

This example illustrates a typical coating composition and process used in this invention. A polyethylene catheter was Freon® wiped, to clean the catheter, and air dried for five minutes. The catheter was then dipped into a coating bath containing 1% POLYOX WSR N-750, 0.18% of DESMODUR IL, and 98.82% of dichloroethane for one minute. This coating solution possessed a polyox/isocyanate (active polyisocyanate compound) and POLYO/(NCO) (active isocyanate groups) ratios of about 11/1 and 69/1, respectively. The catheter was removed from the coating bath and placed in a forced-air oven at 90 degree centigrade for 10 minutes. The coated catheter had a normal plastic feel when dry but became instantly lubricious upon exposure to water or body fluids.

EXAMPLE 2

The degree of lubricity and the abrasion resistance of the coating was measured by the method described in this example. The frictional force generated in pulling a coated catheter through a circular opening punched in a silicone membrane in the presence of water was measured. The inside diameter of the opening was slightly less than the outside diameter of the catheter to produce a tight grip during pulling. The lower the frictional force required to pull the catheter through the opening the greater the lubricity. Measurement of the force was made using a device capable of pulling the catheter through the silicone grommet at a speed of 4.5 inches per minute. An uncoated catheter had a frictional force of 5.0 grams, and the coated catheter of Example 1 provided a frictional force of only 0.4 grams. The same catheter was subsequently abraded against the silicone grommet 10 times and the measurement was repeated. The frictional force of the abraded catheter remained at a low value of 0.4 grams, demonstrating a satisfactory degree of abrasion resistance.

EXAMPLE 3

A polyethylene angioplasty balloon was coated according to the procedure described in Example 1 with the exception that the balloon was inflated to a pressure of about 30 psig during the entire coating operation. The uncoated and coated balloons had frictional force values of 55.4 and 8.4 grams, respectively. After 10 abrasions, the coated balloon retained a low frictional force of 9.4 grams.

EXAMPLE 4

A coating formulation was prepared by mixing in a Waring blender 4.37% of POLYOX WSR N-10, 0.625% of ISONATE 2181, and 95.005% of dichloroethane. The coating solution possessed a POLYOX/isocyanate and POLYOX/(NCO) weight ratios of 7/1 and 30/1, respectively. Polyethylene catheters were coated according to the same procedure described in Example 1. The coated catheter had a frictional force of 4.0 and 3.0 grams before and after 100 abrasions, respectively. The corresponding frictional force values for the uncoated catheter were 16 and 19 grams, respectively.

EXAMPLE 5

Example 4 was repeated with the exception that ISONATE 2181 was replaced with 1.25% of DESMODUR IL. This coating solution possessed a POLYOX/isocyanate and POLYOX/(NCO) weight ratios of about 7/1 and 44/1, respectively. The coated catheter had a frictional force of 5.5 and 5.2 grams before and after 100 abrasions. The corresponding frictional force values for the uncoated catheter were 16 and 19 grams, respectively.

EXAMPLES 6–9

These examples illustrate the usefulness of different molecular weight poly(ethylene oxides) in this invention. All coating solutions had the same POLYOX/isocyanate and POLYOX/(NCO) weight ratios as shown in Example 6. Polyethylene catheters were used in these examples:

| Example | Formulation | Coating Makeup | Fba (grams) | Faa (grams) |
|---|---|---|---|---|
| 6 | POLYOX N-10 | 2 | 5.0 | 5.0 |
| | DESMODUR IL | 0.36 | | |
| | dichloroethane | 97.64 | | |
| | POLYOX/isocyanate 11/1, | | | |
| | POLYOX/(NCO) 69/1 | | | |
| 7 | POLYOX N-80 | 2 | 4.0 | 3.5 |
| | DESMODUR IL | 0.36 | | |
| | dichloroethane | 97.64 | | |
| | POLYOX/isocyanate | | | |
| 8 | POLYOX N-750 | 1 | 3.0 | 3.0 |
| | DESMODUR IL | 0.18 | | |
| | dichloroethane | 98.82 | | |

-continued

| Example | Formulation | Coating Makeup | Fba (grams) | Faa (grams) |
|---|---|---|---|---|
| 9 | POLYOX N-12K | 0.5 | 5.0 | 5.0 |
| | DESMODUR IL | 0.09 | | |
| | dichloroethane | 99.41 | | |
| Control | Uncoated | | 15 | 15 |

Where Fba and Faa stand for frictional force values measured before and after 10 abrasions.

EXAMPLES 10–14

These examples illustrate the performance of this coating applied on polyethylene (a hydrophobic substrate) catheters at various poly(ethylene oxide) (POLYOX WSR N-750)/poly-isocyanate (DESMODUR IL) ratios and solid contents. The coating was applied following the procedure described in Example 1.

| Example | POLYOX/ Formulation | Fba | Faa | POLYOX/ Isocyante | POLYOX/ (NCO) |
|---|---|---|---|---|---|
| 10 | POLYOX N-750 20% | 9.0 | 10 | 9/1 | 57/1 |
| | DESMODUR IL 0..44% | | | | |
| | dichloroethane 97.56% | | | | |
| 11 | POLYOX N-750 2.0% | 6.0 | 6.0 | 13/1 | 81/1 |
| | DESMODUR IL 0.31% | | | | |
| | dichloroethane 97.69% | | | | |
| 12 | POLYOX N-740 3.0% | 7.0 | 7.0 | 11/1 | 69/1 |
| | DESMODUR IL 0.54% | | | | |
| | dichloroethane 96.46% | | | | |
| 13 | IOLYOX N-750 4.0% | 14 | 15 | 9/1 | 57/1 |
| | DESMODUR IL 0.89% | | | | |
| | dichloroethane 95.11% | | | | |
| 14 | POLYOX N-750 4.0% | 8.5 | 8.0 | 13/1 | 81/1 |
| Control | Uncoated | 20 | 20 | | |

EXAMPLES 15–18

These examples illustrate the performance of different monomeric and polymeric polyisocyanates in conjunction with POLYOX WSR N-10 for coating a Tecoflex® (a hydropilic substrate) polyurethane catheter, and the use of a quenching step to eliminate any residual polyisocyanate in the finished coating. In all Examples, 2% POLYOX WSR N-10 and 0.0288% by weight active isocyanate was used. The polyurethane catheter was first wiped with Freon®, and air dried for 5 minutes. The clean catheter was dipped in the coating solution for 30 seconds, air dried for 2 minutes, and oven baked at 80 degrees centigrade for 1 hour. The coated catheter was subsequently dipped in an 0.1N sodium phosphate solution for 1 second, air dried for 2 minutes, and oven baked at 80 degrees centigrade for 2 hours in the presence of water vapor.

| Example | POLYOX/ Formulation Isocyanate | Weight % | Fba | Faa | Polyox/ Isocyanate |
|---|---|---|---|---|---|
| 15 | MONDUR M | 0.089% | 9.2 | 15.3 | 22/1 |
| 16 | MONDUR TD | 0.060% | 7.8 | 14.3 | 22/1 |
| 17 | DESMODUR IL | 0.36% | 5.3 | 5.0 | 11/1 |
| 18 | DESMODUR HL | 0.274% | 2.9 | 2.6 | 12/1 |
| Control | Uncoated catheter | | 15.4 | 15.4 | |

MONDUR M and MONDUR TD are the Miles tradenames for diphenylmethane 4,4'-diisocyanate and toluene diisocyanate, respectively. DESMODUR HL is the Miles trade name for a mixture of adducts derived from toluene diisocyanate and 1,6-hexamethylene diisocyanate. These polyisocyanate adducts are polyisocyanurates. Examples 15–19 demonstrate that polyisocyanurate trimer adducts perform better than the monomeric polyisocyanates in the invention.

EXAMPLES 19–21

These additional examples illustrate the utility of different polyisocyanates for providing a lubricious coating on polyethylene catheter. In all cases, 2% POLYOX WSR N-10, 0.0288% by weight of active isocyanate, and dichloroethane were used. A coating process identical to that described in Example 1 was employed:

| Example | Formulation | Wt. % | POLYOX/ Isocyanate | Fba | Faa |
|---|---|---|---|---|---|
| 19 | DESMODUR IL | 0.36 | 11/1 | 3.8 | 3.9 |
| 20 | MONDUR M | 0.087 | 23/1 | 2.8 | 5.5 |
| 21 | DESMODUR HL | 0.274 | 12/1 | 2.0 | 1.9 |
| Control | Uncoated catheter | | | 23.4 | 23.4 |

Once again the polyisocyanate adducts outperformed the other polyisocyanates.

EXAMPLES 22–23

Tecoflex® polyurethane catheters were used in these examples and were coated according to the procedures described in Example 15. The sliding angle in degrees of the coated catheters were measured according to procedure described in U.S. Pat. No. 4,876,126. Smaller sliding angles demonstrate lower frictional coefficient and greater lubricity.

The formulations and performance of the resultant coated catheters are listed below:

| Example | Formulation* | | Angle-b** | Angle-a*** |
|---|---|---|---|---|
| 22 | DESMODUR IL POLYOW/isocyanate = 11/1 | 0.36% | 3 | 3 |
| 23 | ISONATE 2181 POLYOX/isocy | 0.13% | 3.5 | 3.5 |

| Example | Formulation* | Angle-b** | Angle-a*** |
|---|---|---|---|
|  | anate = 15/1 |  |  |
| Control | Uncoated catheter | 12 | 12 |

*Each coating solution contains 2% by weight of POLYOX WSR N10 in dichloroethane solution.
**Sliding angle measured before any abrasion
***Sliding angle measured after 10 abrasion through a silicone grommet

EXAMPLES 24–25

These examples illustrate the resistance of the coatings prepared in Examples 22–23 to high-energy radiation. Radiation is often used for the sterilization of medical devices. The sliding angle of the coated samples were remeasured after being irradiated with 2.5 millirads of radiation from an electron beam.

| Example | Formulation | Angle-b | Angle-a |
|---|---|---|---|
| 24 | Same as Example 22 | 4 | 4 |
| 25 | Same as Example 23 | 3 | 2.5 |
| Control | Uncoated catheter | 12 | 12 |

EXAMPLES 26–27

These examples illustrate the performance of the lubricious coating of this invention was not affected by the use of different lengths of air-drying time before baking in the oven. Tecoflex® catheters were coated using the coating solution described in Example 6. The coating process described in Example 15 was employed except the dip coated catheters were air dried for different intervals before placing into the baking oven:

| Example | Air Drying Time, (min.) | Fba | Faa |
|---|---|---|---|
| 26 | 30 | 2.1 | 1.5 |
| 27 | 10 | 1.8 | 1.6 |
| 28 | 0 | 1.8 | 1.7 |
| Control | Uncoated catheter | 14.3 | 17.0 |

EXAMPLES 29–30

These examples illustrate the use of solvent mixtures in the coating formulations. Tecoflex® catheters were coated following the process described in Example 17. The coating solution possessed a POLYOX/isocyanate and POLYOX/(NCO) weight ratios of about 11/1 and 69/1, respectively.

| Example | Formulation | Fba | Faa |
|---|---|---|---|
| 29 | POLYOX WSR N-10 2% | 3.7 | 3.5 |
|  | DESMODUR IL 0.36% |  |  |
|  | Toluene 9.7% |  |  |
|  | Dichloroethane 97.94% |  |  |
| 30 | POLYOXWSRN-750 2% | 1.7 | 1.4 |
|  | DESMODUR IL 0.36% |  |  |
|  | Toluene 9.7% |  |  |
|  | Dichloroethane 97.94% |  |  |
| Control | Uncoated catheter | 14.3 | 17 |

EXAMPLES 31–34

These examples demonstrate that the coating solution retains its performance upon aging. The coating formulation and coating process used in these Examples were identical to those described in Example 17. The level of detectable NCO was also measured.

| Example | Age of Coating Solution (days) | Wt. % (NCO) | Fba | Faa |
|---|---|---|---|---|
| 31 | 1 | 0.029 | 1.8 | 1.7 |
| 32 | 3 | 0.01 | 2.4 | 2.4 |
| 33 | 9 | <0.01 | 2.1 | 2.1 |
| 34 | 30 | 0 | 2.9 | 2.7 |
| 35 | 180 | 0 | 4.2 | 4.5 |
| Control |  |  | 16.4 | 16.4 |

The good performance of coating made from the aged coating solution, containing no detectable isocyanate was most unexpected. These results are, however, consistent to our proposed mechanism that good lubricity and abrasion resistance of the coating may result from the formation of a poly(ethylene oxide) and polyurea complex through an in-situ hydrolysis of the polyisocyanate in the system. Thus, as long as there is sufficient polyisocyanate initially present in the coating solution according to the correct poly(ethylene oxide)/isocyanate weight ratio defined in this invention, the coating solution was useful regardless of its age.

EXAMPLES 36–38

These examples illustrate the performance of coating formulations containing a methoxy poly(ethylene glycol) additive. The resultant coatings had improved antiblocking properties without adversely affecting the lubricious nature of the coating. The polyethylene catheter was wiped with Freon® and air dried for 5 minutes. The clean catheter was dipped in the coating solution bath indicated below for one minute and followed by heating in a forced air oven at 90 degree centigrade for a period of 10 minutes.

| Example | Formulation | Weight % | Fba | Faa | POLYOX/Isocyanate |
|---|---|---|---|---|---|
| 36 | POLYOX WSR-12K | 0.5 | 1.6 | 2.5 | 11/1 |
|  | CARBOWAX MPEG 5000 | 0.25 |  |  |  |
|  | DESMODUR IL | 0.09 |  |  |  |
|  | DICHLORO-ETHANE | 99.16 |  |  |  |
| 37 | POLYOX WSR 60K | 0.5 | 1.3 | 1.2 | 11/1 |
|  | CARBOWAX MPEG 5000 | 0.25% |  |  |  |
|  | DESMODUR IL | 0.09% |  |  |  |
|  | Dichloroethane | 99.16% |  |  |  |
| 38 | POLYOX WSR FLOC 309 | 0.5% | 1.4 | 1.2 | 11/1 |
|  | CARBOWAX MPEG 50000 | 0.25% |  |  |  |
|  | DESMO-DURIL | 0.09% |  |  |  |
|  | Dichloroethane | 99.16% |  |  |  |
| Control | Uncoated catheter |  | 29.4 | 29.5 |  |

EXAMPLES 39–45

These examples illustrate the benefit of incorporating CARBOWAX® MPEG-5000 in the coating formulation for resistance against blocking of coated polyethylene catheters when being pressed together in the presence of water or high humidity. Performance against blocking was rated from 1 to 10, 10 being the best and 1 being the worst. Each of the following formulations contained: 0.5% POLYOX WSR® N-3000; 0.09% DESMODUR® IL, the specified amount of CARBOWAX® additive with the balance of the solution being dichloroethane. All catheters were coated following the procedures described in Example 1.

| Example | CARBOWAX MPEG 5000 WT. % | Blocking Resistance | Fba | Faa |
| --- | --- | --- | --- | --- |
| 39 | 0.1 | 5 | 1.8 | 1.6 |
| 40 | 0.2 | 5 | 1.7 | 1.2 |
| 41 | 0.25 | 8 | 1.6 | 1.1 |
| 42 | 0.3 | 7 | 1.8 | 1.6 |
| 43 | 0.4 | 5 | 1.3 | 1.1 |
| 44 | 0.5 | 5 | 0.9 | 0.8 |
| 45 | None | 1 | | |

EXAMPLES 46–48

These examples illustrate the method of quenching a coated polyethylene catheter in an aqueous bath containing a methoxy poly(ethylene oxide) for improved blocking resistance. The catheter was coated according to the procedure described in Example 36. The coated catheter was subsequently dipped into an aqueous solution containing 4% by weight in one of the methoxy poly(ethylene glycol) additives for 1 second, followed by drying at 90 degrees centigrade in a forced air oven for a period of 10 minutes.

| Example | Formulation Resistance | Quenching Bath | Blocking Resistance |
| --- | --- | --- | --- |
| 46 | POLYOX WSR 2050.5% DESMODUR IL 0.09% Dichloroethane 99.41% | CARBOWAX MPEG 5000 | 8 |
| 47 | Same | CARBOWAX MPEG 350 | 10 |
| 48 | Same | Not treated | 2 |

EXAMPLE 49

A pair of polyethylene angioplasty balloons were coated according to the formulation and procedure described in Example 47. The finished balloons were clear, smooth, and gave a normal plastic feel when dry. Upon exposure to water, they became instantly lubricious. When the two balloons were pressed together in the presence of water, they were easily separated without any sign of coating damage. The ability to separate coated articles without damaging the coating is important during the handling, packaging, and sterilization of the articles.

EXAMPLES 50–53

These examples illustrate the better performance characteristics of coatings of this invention in comparison to the teaching of U.S. Pat. No. 5,077,352 (Elton) in Example 3, column 7. Comparisons were made on either Tecoflex® or polyethylene catheters. Examples 50 and 52 were carried out following the procedures described in Examples 3 of Elton. The coating procedure described in Example 17 of this application was used for Example 51, and the procedure described in Example 1 of this application was used for Example 53. While a polyol, such as Mobay MULTRON R-18, was used in the earlier U.S. patent, none is needed for this invention. Dichloroethane was used in all coating solutions in these examples:

| Example | Formulation | Material | Fba | Faa |
| --- | --- | --- | --- | --- |
| 50 | POLYOX WSR N-750 Mobay MONDUR CB-60 POLYOX/poly-isocyanate = 3.5 POLYOX/(NCO) = 20.2 MOBAY MULTRON R-18 Dichloroethane | Tecoflex | 19 | 12.3 |
| 51 | POLYOX WSR N10 02% DESMODUR HL 0.27% POLYOX/polyisocyanate 12.3 POLYOX/(NCO) = 70.5 Dichloroethane | Tecoflex | 2.9 | 2.6 |
| Control | Uncoated catheter | Tecoflex | 17.5 | 17.5 |
| 52 | POLYOX WSR N-750 Mobay MONDUR CB-60 POLYOX/poly-isocyanate = 3.5 POLYOX/(NCO) = 20.2 Mobay MULTRON R-18 Dichloroethane | Polyethylene | 14 | 4.2 |
| 53 | POLYOX WSR N-10 2% DESMODUR HL 0.27% POLYOX/polyisocyanate 12.3 POLYOX/(NCO) = 70.5 Dichloroethane | Polyethylene | 2.0 | 1.9 |
| Control | Uncoated catheter | Polyethylene | 27.5 | 27.5 |

In comparison to the performance of the prior art coatings, coatings of the present invention demonstrate better surface lubricity. In addition, the coatings of the present invention also provide reduced coating swelling which results in better abrasion resistance. The Elton coatings (Examples 50 and 52) provided a swelled coating which became more lubricious upon abrasion because the poorly adhered coating was abraded away. Even after the loosely adhered coating was removed, Elton's coatings were inferior to those of the present invention.

EXAMPLES 54–60

These examples illustrate the performance of the lubricious coating of this invention applied on polyethylene catheter at different poly(ethylene oxide)/polyisocyanate ratios and at different solids contents. The poly(ethylene oxides) and polyisocyanates used in this series of experiments were POLYOX WSR N-10 and ISONATE 2181, respectively. The solvent used was a 1:1 by weight mixture of toluene and dichloroethane. The following coating procedure was employed: (1) the catheter was wiped with a Freon® fluid and air dried; (2) the cleaned catheter was dipped in a coating solution bath for 171 minutes and baked in a forced air oven at 75 degrees centigrade for 1 hour. The coated catheter was then quenched in an 0.1N sodium phosphate solution for 1 second and baked at 75 degrees centigrade for 2 hours in the presence of water vapor:

| Example | POLYOX/ Isocyanate | POLYOX/ Isocyanate Total Wt. % | POLYOX/ (NCO) | Fba | Faa |
| --- | --- | --- | --- | --- | --- |
| 54 | 11/1 | 2 | 48 | 4.5 | 5 |
| 55 | 11/1 | 5 | 48 | 3 | 3 |
| 56 | 9/1 | 5 | 39 | 2.5 | 3 |
| 57 | 7/1 | 5 | 30 | 2.5 | 2.5 |
| 58 | 5.5/1 | 3.5 | 24 | 3 | 4 |

-continued

| Example | POLYOX/ Isocyanate | POLYOX/ Isocyanate Total Wt. % | POLYOX/ (NCO) | Fba | Faa |
|---|---|---|---|---|---|
| 59 | 1/1 | 2 | 4.3 | 8 | 8 |
| 60 | 1/1 | 5 | 4.3 | 4.5 | 5 |
| Control | Uncoated catheter | | | 12 | 14 |

EXAMPLES 61–66

These examples illustrate that the dipping time can be varied as desired without adversely affecting the performance of the resultant coating. Polyethylene catheters were coated following the procedures described in example 54 except for the dipping time. A coating solution containing POLYOX WSR N-10, Isonate 2181, toluene, and dichloroethane at 5% total solids but different POLYOX/isocyanate ratios were used:

| Example | POLYOX/ isocyanate | POLYOX/ (NCO) | Dipping Time | Fba | Faa | Faa* |
|---|---|---|---|---|---|---|
| 61 | 11/1 | 48 | 1 min | 2.5 | 2.5 | 3 |
| 62 | 11/1 | 48 | 1 sec | 2 | 2 | 2.5 |
| 63 | 9/1 | 39 | 1 min | 2.5 | 3 | 2.5 |
| 64 | 9/1 | 39 | 1 sec | 3 | 3 | 3 |
| 65 | 7/1 | 30 | 1 min | 2.5 | 2.5 | 2.5 |
| 66 | 7/1 | 30 | 1 sec | 2.5 | 2.5 | 3.5 |
| Control | Uncoated | | | 13 | 18 | 18 |

Faa*=Friction al force in grams measured after 100 abrasions through the silicone grommet.

EXAMPLES 67–70

These examples compare the performance characteristics of the lubricious coatings prepared according to the present invention, as illustrated by Examples 67 and 69, to those of coatings prepared according to Lambert (U.S. Pat. No. 4,487,808; U.S. Pat. No. 4,459,317), as illustrated by Examples 68 and 70. The procedure of Example 1 in U.S. Pat. No. 4,459,317 was followed in Examples 68 and 70 for coating both Tecoflex® and polyethylene catheters. The procedures described in Examples 6 and 1 in this specification are followed for coating Tecoflex® and polyethylene catheters, respectively:

| Example | Catheter Type | Coating Method | Fba | Faa | Coating Characteristics |
|---|---|---|---|---|---|
| 67 | Tecoflex | Example 6 | 5 | 1.8 | Uniform coating |
| 68 | Tecoflex | Lambert Coating | 7 | 4 | Swollen coating gels; non-uniform coating |
| Control | Tecoflex | Uncoated | 17 | 17 | |
| 69 | Polyethylene | Example 1 | 2 | 1 | |
| 70 | Polyethylene | Lambert Coating | 4 | 2 | Swollen coating gels; non uniform coating |
| Control | Polyethylene | Uncoated | 22.5 | 22.5 | |

In comparison to the two-step coating process described by Lambert, the one-step coating process of this invention is not only simpler and less time consuming, but also provides coating of better uniformity and consistency. Moreover, the Faa was lower for the coatings of the present invention and compared to the two step coating of Lambert for both Tecoflex and Polyethylene catheters. This demonstrates a surprising enhancement in the abrasion resistance of the articles of the present invention which comprise a substantially homogeneous composite coating of poly(ethylene)oxide and polyisocyanate. The latter are important characteristics for precision coatings intended for medical applications, such as for coating angioplasty balloons.

EXAMPLES 71–73

These examples illustrate the utility of this invention for providing a lubricious interluminal surface for a guiding catheter extruded from a polyester-nylon blend (Nylon 11, Nylon 12, and polytetraethylene glycol). This is a particularly difficult application inasmuch as it is necessary to uniformly coat the interior of a device, while maintaining good lubricity and adhesion. The coating solution described in Example 6 was applied according to the following procedure: (1) the coating solution was drawn into the catheter, which is being held vertically above the solution bath, using a suction device such as a syringe and held for 5 minutes; (2) the catheter is subsequently turned upside down to drain the coating solution; and (3) the catheter was dried by blowing preheated hot air at about 75 degrees centigrade through the opening of one end of the catheter while the whole catheter is wound was a coil shape and placed in an oven at 75 degrees centigrade. The coated catheter was then removed from the oven and examined for coating characteristics:

| Example | Drying Time.(hr) | Lubricity | Dye Coverage* |
|---|---|---|---|
| 71 | 1 | Yes | Yes |
| 72 | 1.5 | Yes | Yes |
| 73 | 2 | Yes | Yes |
| Control | Uncoated | No | No |

*The dye-staining test uses a Congo Red dye solution. All of the guiding catheters coated in accordance with the methods of the invention are wetted instantly while the uncoated catheter was not uniformly covered by a coating.

EXAMPLES 74–79

These examples illustrate the range of poly(ethylene oxide)/polyisocyanate ratios that are useful for the purpose of this invention. Coatings prepared at the low end of poly(ethylene oxide)/polyisocyanate ratio may suffer a reduction in lubricity, while those prepared at the high end of the ratio may become uneven and show excessive coating swelling with a resulting lack of coating adhesion. Polyethylene catheters were used in these experiments, and were coated following the same procedures described in example 54. All coating solutions used in the following examples contained 2% by weight total solids.

| Example | POLYOX/ Isocyanate | POLYOX/ (NCO) | Fba | Faa | Coating Characteristics |
|---|---|---|---|---|---|
| 74 | 0.1/1 | 0.44/1 | 10.8 | Erratic | Marginal Lubricity |
| 75 | 0.25/1 | 1.1/11 | 12.3 | Erratic | Marginal Lubricity |
| 76 | 0.5/1 | 2.2/1 | 9.5 | 4.5 | Fair lubricity |
| 77 | 1/1 | 4.4/1 | 8 | 8 | Fair lubricity |
| 78 | 2.5/1 | 11/1 | 5.5 | 4 | Good lubricity |
| 79 | 11/1 | 48/1 | 4.5 | 5 | Good |

-continued

| Example | POLYOX/ Isocyanate | POLYOX/ (NCO) | Fba | Faa | Coating Characteristics |
|---|---|---|---|---|---|
| 80 | 80/1 | 352/1 | 4.5 | 3.2 | Good lubricity |
| 81 | 100/1 | 435/1 | 5.5 | 5 | Uneven coating |
| 82 | 125/1 | 550/1 | 5.3 | 3.2 | Swollen coating |
| 83 | 150/1 | 652/1 | 7.5 | 14 | Uneven coating; excessive swelling |
| Control | Uncoated catheter | | 18 | 18 | |

The results of the above examples demonstrate that it is important to maintain the correct ratios of poly(ethylene oxide) to polyisocyanate defined in this invention to provide a lubricious, and durable coating when the device becomes wet. At a ratio of less than about 0.5/1, the coating exhibits only marginal lubricity. On the other hand, at a ratio of greater than about 125/1 the coating becomes gelatinous when wet and will lose abrasion resistance in the presence of water or body fluids. In the extreme case when no polyisocyanate is used in the initial coating solution, the coating may become discontinuous and non-uniform as a result of inadequate overage on the substrate.

We claim:

1. A method for forming a hydrophilic polymeric coating on a substrate to provide a biocompatible surface having abrasion resistance, said method comprising:
   a) contacting the substrate with a solution of a polyisocyanate and a poly(ethylene oxide) in an inert solvent, said solution comprising less than about 1 weight percent of polyols which can react with the polyisocyanate to form polyurethanes, said percentage based on the total weight of the poly(ethylene oxide), polyisocyanate and said polyol, and said poly(ethylene oxide) having a molecular weight of from about 100,000 to about 8,000,000 grams per gram mole, to provide at least a partially coated substrate; and
   b) drying the at least partially coated substrate to provide a dried coating on said substrate;
wherein the weight ratio of said poly(ethylene oxide) to polyisocyanate ranges from about 0.5/1.0 to about 125/1.

2. The method of claim 1 wherein at least one antimicrobial agent is incorporated in the solution.

3. The method of claim 1 wherein the polyisocyanate is a dimer of an aliphatic or aromatic diisocyanate.

4. The method of claim 1 wherein the substrate is dried by heating at a temperature of from about 30° to 150° C.

5. The method of claim 1 wherein a coating is quenched in an aqueous liquid subsequent to the drying step.

6. The method of claim 1 wherein weight ratio of said poly(ethylene oxide) to polyisocyanate is from about 2.5/1 to about 80/1.

7. The method of claim 1 wherein the dried coating comprises a substantially homogeneous composite of the poly(ethylene oxide) and the polyisocyanate.

8. The method of claim 1 wherein the dried coating comprises less than about 1 weight percent of polyurethanes, said percentage based on the total weight of the dried coating.

9. A method for forming a hydrophilic polymeric coating on a substrate to provide a biocompatible surface having abrasion resistance, said method comprising:
   a) contacting the substrate with a solution of a polyisocyanate and a poly(ethylene oxide) in an inert solvent, said solution comprising less than about 1 weight percent of polyols which can react with the polyisocyanate to form polyurethanes, said percentage based on the total weight of the poly(ethylene oxide), polyisocyanate and said polyol, said poly(ethylene oxide) having a molecular weight of from about 100,000 to about 2,000,000 grams per gram mole, to provide at least a partially coated substrate; and
   b) drying the at least partially coated substrate to provide a dried coating on said substrate comprising a substantially homogenous composite of the poly(ethylene oxide) and the polyisocyanate, and less than about 1 weight percent of polyurethanes, said percentage based on the total weight of the dried coating;
wherein the weight ratio of said poly(ethylene oxide) to polyisocyanate ranges frown about 2.5/1.0 to about 80/1.

* * * * *